(12) United States Patent
Jian et al.

(10) Patent No.: US 12,144,841 B2
(45) Date of Patent: Nov. 19, 2024

(54) FUKE QIANJIN CAPSULE AND QUALITY CONTROL METHOD THEREFOR

(71) Applicant: QIANJIN PHARMACEUTICAL CO., LTD., Hunan (CN)

(72) Inventors: Shun Jian, Hunan (CN); Yun Gong, Hunan (CN); Peng Zhang, Hunan (CN); Fujun Li, Hunan (CN); Yonggen Ling, Hunan (CN); Juanjuan He, Hunan (CN); Kanghua Wang, Hunan (CN); Xiuwei Yang, Hunan (CN)

(73) Assignee: QIANJIN PHARMACEUTICAL CO., LTD., Hunan (CN)

( * ) Notice: Subject to any disclaimer, the term of this patent is extended or adjusted under 35 U.S.C. 154(b) by 0 days.

(21) Appl. No.: 17/293,920

(22) PCT Filed: Jan. 14, 2020

(86) PCT No.: PCT/CN2020/072103
§ 371 (c)(1),
(2) Date: Jan. 10, 2022

(87) PCT Pub. No.: WO2020/098831
PCT Pub. Date: May 22, 2020

(65) Prior Publication Data
US 2022/0143125 A1 May 12, 2022

(30) Foreign Application Priority Data

Nov. 14, 2018 (CN) .......................... 201811356104.0
Nov. 14, 2018 (CN) .......................... 201811356105.5

(51) Int. Cl.
| | | |
|---|---|---|
| A61K 36/758 | (2006.01) |
| A61K 9/16 | (2006.01) |
| A61K 36/19 | (2006.01) |
| A61K 36/232 | (2006.01) |
| A61K 36/29 | (2006.01) |
| A61K 36/48 | (2006.01) |
| A61K 36/738 | (2006.01) |

(52) U.S. Cl.
CPC .......... *A61K 36/758* (2013.01); *A61K 9/1694* (2013.01); *A61K 36/19* (2013.01); *A61K 36/232* (2013.01); *A61K 36/29* (2013.01); *A61K 36/48* (2013.01); *A61K 36/738* (2013.01); *A61K 2236/331* (2013.01); *A61K 2236/333* (2013.01); *A61K 2236/37* (2013.01); *A61K 2236/39* (2013.01); *A61K 2236/51* (2013.01)

(58) Field of Classification Search
None
See application file for complete search history.

(56) References Cited

FOREIGN PATENT DOCUMENTS

| CN | 1298730 | 6/2001 |
| CN | 1170549 C | * 10/2004 |
| CN | 1931272 | 3/2007 |
| CN | 104569192 | 4/2015 |
| CN | 108680673 | 10/2018 |

OTHER PUBLICATIONS

English translation of Gong (CN 104569192 B—2016).*
Godecke (Fitoterapia (2012), vol. 83, pp. 18-32).*
Yang (Journal of Pharmaceutical and Biomedical Analysis (2012), vol. 70, pp. 87-93).*
Jiang Xuexin et al., "Simultaneous Determination of Six Active Components in Fuke Qianjin Tablets by HPLC", China Pharmacist, Dec. 2016, submit with English abstract, pp. 2174-2176.
Linlin Chen et al, "Identification and determination of the major constituents in Traditional Chinese Medicinal formula Danggui-Shaoyao-San by HPLC-DAD-ESI-MS/MS", Journal of Pharmaceutical and Biomedical Analysis, Sep. 2009, pp. 127-137.
Guang-Hua Lu et al, "Quantification of ligustilides in the roots of Angelica sinensis and related umbelliferous medicinal plants by high-performance liquid chromatography and liquid chromatography-mass spectrometry", Journal of Chromatography A, Aug. 2004, pp. 101-107.
Liu Jing et al., "Quality assessment of Caulis Mahoniae by HPLC fingerprint and quantitative analysis", Journal of Henan University (Medical Science), Aug. 2014, submit with English abstract, pp. 170-173.
Wang Kang-Hua et al., "Characteristic fingerprint and multi-components quantitative determination for Fuke Qianjin Capsules by HPLC", China Journal of Chinese Materia Medica, Apr. 2019, submit with English abstract, pp. 1564-1572.
"International Search Report (Form PCT/ISA/210) of PCT/CN2020/072103," mailed on Mar. 30, 2020, with English translation thereof, pp. 1-6.

* cited by examiner

*Primary Examiner* — Susan Hoffman
(74) *Attorney, Agent, or Firm* — JCIPRNET

(57) ABSTRACT

The present invention discloses Fuke Qianjin Capsules and a quality control method therefor. The capsules are made of *Radix et caulis flemingiae, Caulis mahoniae, Herba andrographis, Zanthoxylum dissitum* Hemsl., *Caulis spatholobi, Radix angelicae sinensis, Radix codonopsis*, and *Radix rosa laevigata* as raw materials. Each of the Fuke Qianjin Capsules contains not less than 2.0 mg of Z-ligustilide, and a total amount of andrographolide and dehydroandrographolide is not less than 1.9 mg. A new standard for controlling quality of the Fuke Qianjin Capsules has been established through an analysis of chemical ingredients in the Fuke Qianjin Capsules. This standard adds a variety of core ingredient content to the existing pharmacopoeia standards. According to the Fuke Qianjin Capsules made in this range, the consistency of effects between different batches is more stable. Moreover, the more the types of core ingredients are limited, the more stable the consistency of the drug effect.

5 Claims, No Drawings

FUKE QIANJIN CAPSULE AND QUALITY CONTROL METHOD THEREFOR

CROSS-REFERENCE TO RELATED APPLICATION

This application is a 371 of international application of PCT application serial no. PCT/CN2020/072103, filed on Jan. 14, 2020, which claims the priority benefits of China application no. 201811356104.0, filed on Nov. 14, 2018 and China application no. 201811356105.5, filed on Nov. 14, 2018. The entirety of each of the above mentioned patent applications is hereby incorporated by reference herein and made a part of this specification.

TECHNICAL FIELD

The present invention relates to the technical field of traditional Chinese medicine, and in particular, to Fuke Qianjin Capsules and a quality control method therefor.

RELATED ART

Fuke Qianjin Capsule is a medicine made from 8 medicinal materials of *Radix et caulis flemingiae, Radix rosa laevigata, Herba andrographis, Caulis mahoniae, Zanthoxylum dissitum* Hemsl., *Radix angelicae sinensis, Caulis spatholobi*, and *Radix codonopsis*. Its effect is to clear heat and eliminate dampness, and replenish and benefit qi and blood. It is used for leukorrheal diseases and abdominal pain caused by damp-heat stasis obstruction, symptoms of which include large quantity of leucorrhea, yellow in colour qualitative thick, and stinky, lower abdomen pain, lumbosacral soreness, and fatigued spirit and lack of strength; and chronic pelvic inflammatory disease, endometritis, and chronic cervicitis with the symptoms described above.

In the existing Pharmacopoeia of the People's Republic of China, for the content identification of the Fuke Qianjin Capsules, only total content of andrographolide and dehydroandrographolide is limited. Specifically, in each capsule, based on the total amount of andrographolide ($C_{20}H_{30}O_5$) and dehydroandrographolide ($C_{20}H_{28}O_4$), the content of *Herba andrographis* shall not be less than 1.6 mg. Among compatible ingredients of the Fuke Qianjin Capsule, *Herba andrographis* is only used as the minister drug, and obviously, the existing standards do not regulate other important ingredients in the Fuke Qianjin Capsule, so that it is difficult to control the consistency of effects between different batches of products of the Fuke Qianjin Capsules. Although relatively consistent products have been obtained through formulas and preparation methods, a more effective method is still needed to improve the therapeutic effect of the Fuke Qianjin Capsules.

SUMMARY OF INVENTION

The technical problem to be solved by the present invention is to overcome the above-mentioned shortcomings and deficiencies of the prior art, to provide Fuke Qianjin Capsules and a quality control method therefor. Compared with the existing Fuke Qianjin Capsules, the Fuke Qianjin Capsules prepared by the quality control method of the present invention are more stable in terms of effect consistency, and have a better clinical treatment effect than the existing Fuke Qianjin Capsules.

An objective of the present invention is to provide a quality control method for Fuke Qianjin Capsules.

Another objective of the present invention is to provide Fuke Qianjin Capsules.

The above-described objectives of the present invention are realized by the following technical solutions.

A quality control method for Fuke Qianjin Capsules, including the following steps:

using *Radix et caulis flemingiae, Radix rosa laevigata, Herba andrographis, Radix angelicae sinensis, Caulis mahoniae, Zanthoxylum dissitum* Hemsl., *Caulis spatholobi* and *Radix codonopsis* as raw materials;

S1, first extracting the *Radix angelicae sinensis* by ethanol percolating to prepare a cream;

S2, extracting the *Herba andrographis* by ethanol refluxing to prepare a cream;

S3, boiling and extracting the *Caulis mahoniae* and the *Zanthoxylum dissitum* Hemsl. with water twice, after filtering, combining two filtrates to prepare a cream;

S4, boiling and extracting the *Radix et caulis flemingiae*, the *Radix rosa laevigata*, the *Caulis spatholobi*, and the *Radix codonopsis* with water once and then filtering, boiling with water a filtered residue with a *Radix angelicae sinensis* residue produced in the step S1, an *Herba andrographis* residue produced in the step S2 and a *Caulis mahoniae* and *Zanthoxylum dissitum* Hemsl. residue produced in the step S3 together, filtering, combining filtrates to prepare a cream; and S5, combining the four creams of the steps S1, S2, S3, S4, mixing, controlling a content of at least one of Z-ligustilide and Z-3-butylidenephthalide, and a total amount of andrographolide and dehydroandrographolide in the cream to reach a standard content, spray drying, and then pelletizing, canning to obtain the Fuke Qianjin Capsules. According to the 2015 edition of the Pharmacopoeia of the People's Republic of China, the mass of each Fuke Qianjin Capsule is 0.4 mg.

In the Fuke Qianjin Capsules, the *Radix et caulis flemingiae* and the *Caulis mahoniae* clear heat and remove toxicity, eliminate dampness and arrest leucorrhoea, and together serve as a sovereign drug. The *Herba andrographis* and the *Zanthoxylum dissitum* Hemsl. clear heat and remove toxicity, cool the blood and relieve swelling, eliminate dampness and arrest leucorrhoea, and serve as a minister drug. The *Caulis spatholobi* and the *Radix angelicae sinensis* nourish the blood and promote blood circulation. The *Radix codonopsis* benefits qi and strengthens spleen, and promotes transportation and digestion of water-dampness to arrest leucorrhoea. The *Radix rosa laevigata* arrests spontaneous emission and leucorrhoea, and serves as an assistant drug.

Traditional Chinese medicine compound is a hierarchical and structured organic whole. Its effect is not a simple addition of individual medicines, but a result of the mutual cooperation of multiple active ingredients. In the existing Pharmacopoeia, the standard regulations for the Fuke Qianjin Capsules only limit that andrographolide and dehydroandrographolide are from the minister drug (from *Herba andrographis*), but do not limit types and contents of other active ingredients. In the actual production process, in quality detection and control, only andrographolide and dehydroandrographolide were detected, but types and contents of other active ingredients were not detected. As we all know, a content of an active ingredient in an extract of a traditional Chinese medicinal material is affected by the planting area of the medicinal material and the extraction method, so even if the extract is prepared according to the same raw material formula, a content of a specific active ingredient is not the same. Therefore, the content of other active ingredients that is not detected between different batches of the Fuke Qianjin Capsules are not uniform, resulting in large differences in their efficacy.

In order to ensure that the prepared Fuke Qianjin Capsules have the same efficacy in the actual production process, the inventors have found after many experiments that in addition to andrographolide and dehydroandrographolide, by controlling the contents of the six active ingredients of genistin, jatrorrhizine, palmatine, berberine, Z-ligustilide and Z-3-butylidenephthalide in the product within a certain range, the effect of the produced product is better, the efficacy of different batches is consistent, and the clinical treatment effect is improved. Due to the various influencing factors in a preparation process of a traditional Chinese medicine, the content control of core ingredients in the traditional Chinese medicine can overcome the problem of fluctuations in ingredient content between different batches. As a result, a new quality control method for the Fuke Qianjin Capsules is proposed. Using the quality control method, it can ensure that the contents of the five active ingredients in different batches of products are relatively consistent, and the consistency of the product's efficacy is relatively stable.

Preferably, in the step S5, per milligram of the cream, the content of the Z-ligustilide is not less than 0.01 mg and/or the content of the Z-3-butylidenephthalide is not less than 0.00017 mg, and the total amount of the andrographolide and the dehydroandrographolide is not less than 0.01 mg.

Preferably, in the step S5, per milligram of the cream, the content of the Z-ligustilide is not less than 0.015 mg and/or the content of the Z-3-butylidenephthalide is not less than 0.00025 mg, and the total amount of the andrographolide and the dehydroandrographolide is not less than 0.015 mg.

Preferably, in the step S5, per milligram of the cream, the content of the Z-ligustilide is 0.0165 mg to 0.022 mg and/or the content of the Z-3-butylidenephthalide is 0.00036 mg to 0.0006 mg, and the total amount of the andrographolide and the dehydroandrographolide is not less than 0.02 mg.

A quality control method for Fuke Qianjin Capsules, including the following steps:
  using *Radix et caulis flemingiae, Radix rosa laevigata, Herba andrographis, Radix angelicae sinensis, Caulis mahoniae, Zanthoxylum dissitum* Hemsl., *Caulis spatholobi* and *Radix codonopsis* as raw materials;
  S1, first extracting the *Radix angelicae sinensis* by ethanol percolating to prepare a cream;
  S2, extracting the *Herba andrographis* by ethanol refluxing to prepare a cream;
  S3, boiling and extracting the *Caulis mahoniae* and the *Zanthoxylum dissitum* Hemsl. with water twice, after filtering, combining two filtrates to prepare a cream;
  S4, boiling and extracting the *Radix et caulis flemingiae*, the *Radix rosa laevigata, Caulis spatholobi*, and the *Radix codonopsis* with water once and then filtering, boiling with water a filtered residue with a *Radix angelicae sinensis* residue produced in the step S1, an *Herba andrographis* residue produced in the step S2 and a *Caulis mahoniae* and *Zanthoxylum dissitum* Hemsl. residue produced in the step S3 together, filtering, combining filtrates to prepare a cream; and
  S5, combining the four creams of the steps S1, S2, S3, S4, mixing, controlling a content of Z-ligustilide, and/or a content of Z-3-butylidenephthalide, and/or a content of genistin, and/or a content of jatrorrhizine, and/or a content of palmatine, and/or a content of berberine, and a total amount of andrographolide and dehydroandrographolide in the cream to reach a standard content, spray drying, and then pelletizing, canning to obtain the Fuke Qianjin Capsules.

Preferably, in the step S5, per milligram of the cream, the content of the genistin is not less than 0.00015 mg, the content of the jatrorrhizine is not less than 0.0004 mg, the content of the palmatine is not less than 0.00038 mg, the content of the berberine is not less than 0.0004 mg, the content of the Z-ligustilide is not less than 0.01 mg, the content of the Z-3-butylidenephthalide is not less than 0.00017 mg, and the total amount of the andrographolide and the dehydroandrographolide is not less than 0.01 mg.

Preferably, in the step S5, per milligram of the cream, the content of the genistin is not less than 0.0002 mg, the content of the jatrorrhizine is not less than 0.0006 mg, the content of the palmatine is not less than 0.0006 mg, the content of the berberine is not less than 0.0006 mg, the content of the Z-ligustilide is not less than 0.015 mg, the content of the Z-3-butylidenephthalide is not less than 0.00025 mg, and the total amount of the andrographolide and the dehydroandrographolide is not less than 0.015 mg.

Preferably, in the step S5, it is controlled that per milligram of the cream, the content of the genistin is 0.0025 mg to 0.0035 mg, the content of the jatrorrhizine is 0.009 mg to 0.015 mg, the content of the palmatine is 0.007 mg to 0.01 mg, the content of the berberine is 0.0085 mg to 0.01 mg, the content of the Z-ligustilide is 0.0165 mg to 0.022 mg, the content of the Z-3-butylidenephthalide is 0.00036 mg 0.0006 mg, and the total amount of the andrographolide and the dehydroandrographolide is not less than 0.02 mg.

Preferably, in each of the Fuke Qianjin Capsules prepared by said method (according to the 2015 edition of the Pharmacopoeia of the People's Republic of China, the mass of each Fuke Qianjin Capsule is 0.4 mg), the genistin is not less than 0.025 mg, the jatrorrhizine is not less than 0.08 mg, the palmatine is not less than 0.06 mg, the berberine is not less than 0.08 mg, the Z-ligustilide is not less than 2.0 mg, the Z-3-butylidenephthalide is not less than 0.03 mg, and the total amount of the andrographolide and the dehydroandrographolide is not less than 1.6 mg.

Preferably, in each of the Fuke Qianjin Capsules prepared by said method (according to the 2015 edition of the Pharmacopoeia of the People's Republic of China, the mass of each Fuke Qianjin Capsule is 0.4 mg), the genistin is not less than 0.025 mg, the jatrorrhizine is not less than 0.08 mg, the palmatine is not less than 0.060 mg, the berberine is not less than 0.08 mg, the Z-ligustilide is not less than 2.0 mg, the Z-3-butylidenephthalide is not less than 0.03 mg, and the total amount of the andrographolide and the dehydroandrographolide is not less than 1.9 mg.

Preferably, in each of the Fuke Qianjin Capsules prepared by said method (according to the 2015 edition of the Pharmacopoeia of the People's Republic of China, the mass of each Fuke Qianjin Capsule is 0.4 mg), the genistin is not less than 0.032 mg, the jatrorrhizine is not less than 0.12 mg, the palmatine is not less than 0.075 mg, the berberine is not less than 0.12 mg, the Z-ligustilide is not less than 2.6 mg, the Z-3-butylidenephthalide is not less than 0.04 mg, and the total amount of the andrographolide and the dehydroandrographolide is not less than 2.5 mg.

Preferably, the total amount of the andrographolide and the dehydroandrographolide in each of the Fuke Qianjin Capsules is not less than 3.5 mg.

Preferably, each of the Fuke Qianjin Capsules prepared by said method contains 0.04 mg to 0.06 mg of the genistin, 0.165 mg to 0.20 mg of the jatrorrhizine, 0.090 mg to 0.130 mg of the palmatine, 0.13 mg to 0.18 mg of the berberine, 3.0 mg to 3.65 mg of the Z-ligustilide, 0.065 mg to 0.105 mg of the Z-3-butylidenephthalide, and the total amount of the andrographolide and the dehydroandrographolide is not less than 3.5 mg.

Preferably, in the step S5, said controlling makes the contents of the genistin, the jatrorrhizine, the palmatine, the berberine, the Z-ligustilide and the Z-3-butylidenephthalide after the 4 creams in the steps S1 to S4 are mixed reach a required range by adjusting an extraction process of the steps S1, S2, S3, S4 or a source of the raw materials.

A detection method adopted in the step S5 is HPLC detection.

Preferably, a preparation process of described in the step S5 is: taking 1 g cream, adding 200 mL of 75% formalin to dissolve, and then taking 2 mL of a dissolving solution and diluting to 10 mL with 75% formalin, passing through a 0.45 μm microporous membrane, and taking the filtrate as a solution to be tested; using Kromasil 100-5-C18 chromatographic column (250 mm×4.6 mm, 5 μm), with mobile phases using acetonitrile as an A phase and 0.1% phosphoric acid aqueous solution as a B phase, gradient eluting, with a flow rate being 1.0 mL·min-1, a detection wavelength being 254 nm, a column temperature being (30±0.5)° C., and an injection volume being 10 μL.

Preferably, the method of the step S1 is that crushing the *Radix angelicae sinensis* into coarse powder, passing through an 8-mesh sieve, infiltrating with ethanol with a mass concentration of 70%, placing in a percolation cylinder, immersing for 48 hours, percolating at a rate of 0.2 mL/min, and collecting 10 times the amount of percolation liquid, concentrating to obtain the *Radix angelicae sinensis* cream with a relative density of 1.1 (80° C.).

Preferably, the method of the step S2 is that: crushing the *Herba andrographis* through a 100-mesh sieve, adding ethanol with a mass concentration of 90% according to a material-to-liquid ratio of 1:9 to extract by heating and reflux, refluxing for 4 hours, separating an extracting solution, and then refluxing the residue according to a material-liquid ratio of 1:8 for 3.5 hours, separating an extract solution, combining the two extract solutions, filtering, and concentrating to obtain the *Herba andrographis* cream with a relative density of 1.1 (80° C.).

Preferably, the method of the step S3 is that boiling and extracting the *Caulis mahoniae* and the *Zanthoxylum dissitum* Hemsl. with water twice, adding water 12 times the total weight of the two-flavored Chinese medicine for the first time and decocting for 4 hours, releasing an decoction, and adding water 10 times the amount of water for the second time and decocting for 3 hours, releasing an decoction, combining the decoctions, filtering, and concentrating an filtrate to obtain a cream with a relative density of 1.1 (80° C.).

Preferably, the method of the step S4 is that boiling the *Radix et caulis flemingiae*, the *Radix rosa laevigata*, the *Caulis spatholobi*, and the *Radix codonopsis* according to a material-to-liquid ratio of 1:10 for 3.5 hours, extracting once and filtering, and concentrating an filtrate to obtain a cream with a relative density of 1.1 (80° C.), combining the filtered residue with the *Radix angelicae sinensis* residue generated in step S2, the *Herba andrographis* residue generated in step S2, and the residue generated in step S3, and adding 4 times the volume of water to decoct for 3 hours, filtering, and concentrating to obtain a cream with a relative density of 1.1 (80° C.).

Preferably, the genistin is from the raw medicinal material *Radix et caulis flemingiae* of the Fuke Qianjin Capsules, the jatrorrhizine, the palmatine and the berberine are from the raw medicinal material *Caulis mahoniae* of the Fuke Qianjin Capsules, the Z-ligustilide and the Z-3-butylidenephthalide are from the raw medicinal material *Radix angelicae sinensis* of the Fuke Qianjin Capsules, and the andrographolide and the dehydroandrographolide are from the raw medicinal material *Herba andrographis* of the Fuke Qianjin Capsules.

Preferably, dosage of the *Radix angelicae sinensis*, the *Radix codonopsis*, the *Herba andrographis* and the *Zanthoxylum dissitum* Hemsl. is each 9% of a total amount of the medicinal materials of the Fuke Qianjin Capsules; and dosage of the *Radix rosa laevigata*, the *Caulis spatholobi*, the *Caulis mahoniae* and the *Radix et caulis flemingiae* is each 16% of the total amount of the medicinal materials of the Fuke Qianjin Capsules.

The present invention also claims for protection for Fuke Qianjin Capsules prepared by the above quality control method and use thereof in preparation of drugs for treating a gynecological disease.

Preferably, the gynecological disease is chronic pelvic inflammatory disease, chronic adnexitis or endometritis.

The present invention also claims for protection for Fuke Qianjin Capsules, which are made of *Radix et caulis flemingiae, Caulis mahoniae, Herba andrographis, Zanthoxylum dissitum* Hemsl., *Caulis spatholobi, Radix angelicae sinensis, Radix codonopsis* and *Radix rosa laevigata* as raw materials, each of the Fuke Qianjin Capsules contains not less than 2.0 mg of Z-ligustilide; preferably contains 2.6 mg of the Z-ligustilide; and more preferably contains 3.0 mg to 3.65 mg of the Z-ligustilide;

and a total amount of andrographolide and dehydroandrographolide is not less than 1.9 mg; preferably, the total amount of the andrographolide and the dehydroandrographolide is not less than 2.5 mg; and preferably, the total amount of the andrographolide and the dehydroandrographolide is not less than 3.5 mg.

Fuke Qianjin Capsules, made of *Radix et caulis flemingiae, Caulis mahoniae, Herba andrographis, Zanthoxylum dissitum* Hemsl., *Caulis spatholobi, Radix angelicae sinensis, Radix codonopsis* and *Radix rosa laevigata* as raw materials, each of the Fuke Qianjin Capsules contains not less than 0.03 mg of Z-3-butylidenephthalide; preferably contains not less than 0.04 mg of the Z-3-butylidenephthalide; and preferably contains 0.065 mg to 0.105 mg of the Z-3-butylidenephthalide;

and a total amount of andrographolide and dehydroandrographolide is not less than 1.9 mg; preferably, the total amount of the andrographolide and the dehydroandrographolide is not less than 2.5 mg; and preferably, the total amount of the andrographolide and the dehydroandrographolide is not less than 3.5 mg.

Fuke Qianjin Capsules, made of *Radix et caulis flemingiae, Caulis mahoniae, Herba andrographis, Zanthoxylum dissitum* Hemsl., *Caulis spatholobi, Radix angelicae sinensis, Radix codonopsis* and *Radix rosa laevigata* as raw materials, each of the Fuke Qianjin Capsules contains not less than 2.0 mg of Z-ligustilide, and not less than 0.03 mg of Z-3-butylidenephthalide; and a total amount of andrographolide and dehydroandrographolide is not less than 1.9 mg;

preferably each of the Fuke Qianjin Capsules contains not less than 2.6 mg of the Z-ligustilide, not less than 0.04 mg of the Z-3-butylidenephthalide, and the total amount of the andrographolide and the dehydroandrographolide is not less than 2.5 mg;

preferably each of the Fuke Qianjin Capsules contains 3.0 mg to 3.65 mg of the Z-ligustilide, and 0.065 mg to 0.105 mg of the Z-3-butylidenephthalide, and the total amount of the andrographolide and the dehydroandrographolide is not less than 3.5 mg.

Fuke Qianjin Capsules, made of *Radix et caulis flemingiae, Caulis mahoniae, Herba andrographis, Zanthoxylum dissitum* Hemsl., *Caulis spatholobi, Radix angelicae sinensis, Radix codonopsis* and *Radix rosa laevigata* as raw materials, each of the Fuke Qianjin Capsules (according to the 2015 edition of the Pharmacopoeia of the People's Republic of China, the mass of each Fuke Qianjin Capsule is 0.4 mg) contains not less than 0.025 mg of genistin, not less than 0.08 mg of jatrorrhizine, not less than 0.060 mg of palmatine, not less than 0.08 mg of berberine, not less than 2.0 mg of Z-ligustilide, and not less than 0.03 mg of Z-3-butylidenephthalide, and a total amount of the andrographolide and the dehydroandrographolide is not less than 1.9 mg.

Preferably, each of the Fuke Qianjin Capsules contains not less than 0.032 mg of the genistin, not less than 0.12 mg of the jatrorrhizine, not less than 0.075 mg of the palmatine, not less than 0.12 mg of the berberine, not less than 2.6 mg of the Z-ligustilide, and not less than 0.04 mg of the Z-3-butylidenephthalide, and the total amount of the andrographolide and the dehydroandrographolide is not less than 2.5 mg.

Preferably, in each of the Fuke Qianjin Capsules, the total amount of the andrographolide and the dehydroandrographolide is not less than 3.5 mg.

Preferably, each of the Fuke Qianjin Capsules contains 0.04 mg to 0.06 mg of the genistin, 0.165 mg to 0.20 mg of the jatrorrhizine, 0.090 mg to 0.130 mg of the palmatine, 0.13 mg to 0.18 mg of the berberine, 3.0 mg to 3.65 mg of the Z-ligustilide, and 0.065 mg to 0.105 mg of the Z-3-butylidenephthalide, and the total amount of the andrographolide and the dehydroandrographolide is not less than 3.5 mg.

Preferably, each of the Fuke Qianjin Capsules contains 0.045 mg to 0.056 mg of the genistin, 0.175 mg to 0.195 mg of the jatrorrhizine, 0.10 mg to 0.130 mg of the palmatine, 0.16 mg to 0.178 mg of the berberine, 3.30 mg to 3.65 mg of the Z-ligustilide, 0.080 mg to 0.105 mg of the Z-3-butylidenephthalide, 2.5 mg to 4.15 mg of the andrographolide and 1.0 mg to 1.3 mg of the dehydroandrographolide.

Additionally preferably, the contents of the genistin, the jatrorrhizine, the palmatine, the berberine, the Z-ligustilide, the Z-3-butylidenephthalide, and the total amount of the andrographolide and the dehydroandrographolide are determined by HPLC detection.

Preferably, a test sample for the HPLC detection is prepared by the following method: taking out 1.00 g of contents of Fuke Qianjin Capsules and placing in a triangular flask, accurately adding 20 mL of 75% formalin, and ultrasonically extracting for (30±5) minutes, after cooling to room temperature, using 75% formalin to make up a mass loss, passing through a 0.45 μm microporous membrane, and taking the filtrate as a solution to be tested.

Preferably, the HPLC detection is performed according to the following conditions: using Kromasil 100-5-C18 chromatographic column (250 mm×4.6 mm, 5 μm), with mobile phases using acetonitrile as an A phase and 0.1% phosphoric acid aqueous solution as a B phase, gradient eluting, with a flow rate being 1.0 mL·min-1, a detection wavelength being 254 nm, a column temperature being (30±0.5)° C., and an injection volume being 10 μL.

Preferably, the genistin is from the raw medicinal material *Radix et caulis flemingiae* of the Fuke Qianjin Capsules, the jatrorrhizine, the palmatine and the berberine are from the raw medicinal material *Caulis mahoniae* of the Fuke Qianjin Capsules, the Z-ligustilide and the Z-3-butylidenephthalide are from the raw medicinal material *Radix angelicae sinensis* of the Fuke Qianjin Capsules, and the andrographolide an the dehydroandrographolide are from the raw medicinal material *Herba andrographis* of the Fuke Qianjin Capsules.

Preferably, dosage of the *Radix angelicae sinensis*, the *Radix codonopsis*, the *Herba andrographis* and the *Zanthoxylum dissitum* Hemsl. is each 9% of a total amount of the medicinal materials of the Fuke Qianjin Capsules; and dosage of the *Radix rosa laevigata*, the *Caulis spatholobi*, the *Caulis mahoniae* and the *Radix et caulis flemingiae* is each 16% of the total amount of the medicinal materials of the Fuke Qianjin Capsules.

The present invention also claims for protection for Fuke Qianjin Capsules prepared by the above quality control method and use thereof in preparation of drugs for treating a gynecological disease. Preferably, the gynecological disease is chronic pelvic inflammatory disease, chronic adnexitis or endometritis.

Compared with the prior art, the present invention has the following beneficial effects.

The present invention has established a new standard for controlling quality of the Fuke Qianjin Capsules through an analysis of chemical ingredients in the Fuke Qianjin Capsules. This standard adds a variety of core ingredient content to the existing pharmacopoeia standards. According to the Fuke Qianjin Capsules made in this range, the consistency of effects between different batches is more stable. Moreover, the more the types of core ingredients are limited, the more stable the consistency of the drug effect. Compared with the prior art, the Fuke Qianjin Capsules provided by the present invention has a better clinical treatment effect.

Further, in addition to controlling the contents of andrographolide and dehydroandrographolide in the product, a detection process is added to the preparation process of the product to control the contents of genistin, jatrorrhizine, palmatine, beberine, Z-ligustilide and Z-3-butylidenephthalide in the product to ensure that the contents of these 6 active ingredients in the product is within a certain range, thereby ensuring that the consistency of the efficacy of the product between different batches is more stable.

At the same time, the present invention adopts HPLC method for detection, which not only has high accuracy of detection results, but also rapid and simple detection process, which is convenient for the actual production process of the Fuke Qianjin Capsules of the present invention to simultaneously detect and monitor contents of multiple active ingredients in the original preparation process, which is conducive to the implementation of the new standard.

DESCRIPTION OF EMBODIMENTS

The present invention is further described in detailed below in combination with specific embodiments, which are only used to explain the present invention, and are not used to limit the scope of the present invention. Unless otherwise specified, test methods used in the following embodiments are conventional methods. The materials and reagents used, unless otherwise specified, are commercially available reagents and materials.

Embodiment 1 Fuke Qianjin Capsules

Formula of Fuke Qianjin Capsules: dosage of *Radix angelicae sinensis, Radix codonopsis, Herba andrographis* and *Zanthoxylum dissitum* Hemsl. was each 9% of a total amount of the medicinal materials; and dosage of *Radix rosa laevigata*, *Caulis spatholobi*, *Caulis mahoniae* and *Radix et caulis flemingiae* was each 16% of the total amount of the medicinal materials. The total amount of the medicinal materials was 500 kg. The product was prepared by the following methods:

(1) the *Radix angelicae sinensis* was first extracted by ethanol percolating to prepare a cream: the *Radix angelicae sinensis* was crushed into coarse powder, passed through an 8-mesh sieve, infiltrated with ethanol with a mass concentration of 70%, placed in a percolation cylinder, immersed for 48 hours, percolated at a rate of 0.2 mL/min, and collected 10 times the amount of percolation liquid, concentrated to obtain a relative density of 1.1 (80° C.), which was the *Radix angelicae sinensis* cream;

(2) the *Herba andrographis* was extracted by ethanol refluxing to prepare a cream: the *Herba andrographis* was crushed through a 100-mesh sieve, ethanol with a mass concentration of 90% was added according to a material-to-liquid ratio of 1:9 to extract by heating and reflux, refluxed for 4 hours, an extracting solution was separated, and then the residue was refluxed according to a material-liquid ratio of 1:8 for 3.5 hours, an extract solution was separated, the two extract solutions was combined, filtered, and concentrated to obtain a relative density of 1.1 (80° C.), which was the *Herba andrographis* cream;

(3) the *Caulis mahoniae* and the *Zanthoxylum dissitum* Hemsl. were boiling extracted with water twice, water 12 times the total weight of the two-flavored Chinese medicine was added for the first time and decocted for 4 hours, an decoction was released; and water 10 times the total weight of the two-flavored Chinese medicine was added for the second time and decocted for 3 hours, an decoction was released, the decoctions were combined, filtered, and an filtrate was concentrated to a relative density of 1.1 (80° C.) to obtain a cream of the two medicines;

(4) the *Radix et caulis flemingiae*, the *Radix rosa laevigata*, the *Caulis spatholobi*, and the *Radix codonopsis* were boiled according to a material-to-liquid ratio of 1:10 for 3.5 hours, extracted once and filtered, and an filtrate was concentrated to obtain a cream with a relative density of 1.1 (80° C.); then the filtered residue with the *Radix angelicae sinensis* residue generated in step S2, the *Herba andrographis* residue generated in step S2, and the residue generated in step S3 were combined, and 4 times the volume of water was added to decoct for 3 hours, filtered, and an filtrate was concentrated to obtain a cream with a relative density of 1.1 (80° C.); and (5) the four creams of the (1), (2), (3), (4) were combined and mixed for HPLC detection, per milligram of cream, a content of Z-ligustilide was controlled not less than 0.01 mg, and/or a content of Z-3-butylidenephthalide was controlled not less than 0.00017 mg, and/or a content of genistin was controlled not less than 0.00015 mg, and/or a content of jatrorrhizine was controlled not less than 0.0004 mg, and/or a content of palmatine was controlled not less than 0.0038 mg, and/or a content of berberine was controlled not less than 0.0004 mg, and a total amount of andrographolide and dehydroandrographolide was controlled not less than 0.01 mg, spray drying, pelletizing, and canning were carried out to obtain the Fuke Qianjin Capsules, and according to the 2015 edition of the Pharmacopoeia of the People's Republic of China, the content of each Fuke Qianjin Capsule was 0.4 g.

When in the detection result of the mixed cream in the step (5), the content of any one of the 6 active ingredients (Z-ligustilide, Z-3-butylidenephthalide, genistin, jatrorrhizine, palmatine, berberine) failed to meet the above conditions, a part of sample was reserved for use.

When in the detection result of the mixed cream in the step (5), the contents of 6 active ingredients (Z-ligustilide, Z-3-butylidenephthalide, genistin, jatrorrhizine, palmatine, berberine) all failed to meet the above conditions, it was a comparative sample and was reserved for use.

The cause of the cream with fluctuating active ingredient content was analyzed, which may be caused by the difference in content of the active ingredients of the raw materials between different batches.

The Fuke Qianjin Capsules were prepared according to the above method, multiple batches of products were randomly selected from a long-term, large number of products, and HPLC detection was performed on each batch of the Fuke Qianjin Capsule products.

Preparation of a solution to be tested: Fuke Qianjin Capsules were randomly selected, 1.0 g of contents was taken out and placed in a triangular flask with a ground stopper, 20 mL of 75% formalin was accurately added, weighing was performed, ultrasonic extraction was performed for 30 minutes, after cooled to room temperature, 75% formalin was used to make up a mass loss, after passing through a 0.45 μm microporous membrane, a filtrate was taken as the solution to be tested.

Kromasil 100-5-C18 chromatographic column (250 mm×4.6 mm, 5 μm) was used, mobile phases were acetonitrile (A phase) and 0.1% phosphoric acid aqueous solution (B phase), gradient elution was performed, with a flow rate of 1.0 mL·min-1, a detection wavelength of 254 nm, a column temperature of 30° C., and an injection volume of 10 μL.

Embodiment 2

Fuke Qianjin Capsules, the steps (1) to (4) in the preparation process thereof are the same as in Embodiment 1, and the difference from Embodiment 1 is that in the step (5), per milligram of the cream, the content of the Z-ligustilide was controlled not less than 0.015 mg, and/or the content of the Z-3-butylidenephthalide was controlled not less than 0.00025 mg, and/or the content of the genistin was controlled not less than 0.002 mg, and/or the content of the jatrorrhizine was controlled not less than 0.006 mg, and/or the content of the palmatine was controlled not less than 0.006 mg, and/or the content of the berberine was controlled not less than 0.006 mg, and the total amount of the andrographolide and the dehydroandrographolide was controlled not less than 0.015 mg; spray drying, pelletizing and canning were carried out to obtain the Fuke Qianjin Capsules, and according to the 2015 edition of the Pharmacopoeia of the People's Republic of China, the content of each Fuke Qianjin Capsule was 0.4 g.

The Fuke Qianjin Capsules were prepared according to the above method, multiple batches of products were randomly selected from a long-term, large number of products, and detection was performed on each batch of the Fuke Qianjin Capsules according to the HPLC detection method in Embodiment 1.

The HPLC detection results of the 6 batches randomly selected from the multiple batches of samples detected in Embodiment 1 and the 6 batches randomly selected in the Embodiment 2 are shown in Table 1.

TABLE 1

Contents of eight ingredients in Fuke Qianjin Capsules prepared in the Embodiments 1 and 2 (μg/capsule)

| | | genistin/μg | jatrorrhizine/μg | palmatine/μg | berberine/μg | andrographolide/μg | dehydroandrographolide/μg | Z-ligustilide/μg | Z-3-butylidenephthalide/μg |
|---|---|---|---|---|---|---|---|---|---|
| Embodiment 1 | Batch 1 | 55.04 ± 0.12 | 82.15 ± 3.65 | 84.68 ± 2.46 | 171.65 ± 0.45 | 3055.64 ± 6.47 | 1015.15 ± 0.36 | 3462.21 ± 9.54 | 28.65 ± 0.25 |
| | Batch 2 | 30.34 ± 0.11 | 115.41 ± 4.16 | 92.11 ± 0.35 | 82.30 ± 0.41 | 3121.01 ± 11.12 | 623.90 ± 1.14 | 2123.51 ± 8.46 | 27.34 ± 1.65 |
| | Batch 3 | 25.31 ± 1.32 | 102.14 ± 1.03 | 102.34 ± 0.56 | 135.22 ± 2.16 | 1557.16 ± 4.65 | 982.06 ± 1.54 | 1910.41 ± 10.31 | 75.32 ± 0.81 |
| | Batch 4 | 28.40 ± 0.71 | 160.25 ± 3.24 | 61.32 ± 1.22 | 127.37 ± 0.12 | 2874.51 ± 2.34 | 414.02 ± 2.35 | 1944.01 ± 12.04 | 51.05 ± 1.61 |
| | Batch 5 | 32.91 ± 0.46 | 95.05 ± 1.19 | 126.41 ± 1.57 | 112.65 ± 0.31 | 2856.02 ± 4.12 | 882.28 ± 5.32 | 2524.68 ± 11.74 | 72.32 ± 0.28 |
| | Batch 6 | 44.24 ± 1.30 | 130.24 ± 2.53 | 119.02 ± 0.22 | 154.21 ± 0.11 | 3546.14 ± 1.32 | 1263.02 ± 3.41 | 3255.21 ± 9.36 | 53.66 ± 0.14 |
| Embodiment 2 | Batch 1 | 47.65 ± 0.44 | 180.07 ± 1.25 | 116.35 ± 0.32 | 153.22 ± 3.54 | 3274.21 ± 8.36 | 1135.12 ± 6.34 | 3196.3 ± 8.36 | 72.23 ± 0.32 |
| | Batch 2 | 45.86 ± 0.23 | 155.3 ± 0.49 | 91.35 ± 0.84 | 172.99 ± 0.53 | 2564.15 ± 2.92 | 751.89 ± 5.28 | 3101.09 ± 5.63 | 79.67 ± 0.32 |
| | Batch 3 | 38.32 ± 0.99 | 174.5 ± 0.56 | 115.8 ± 0.63 | 160.03 ± 0.31 | 1817.44 ± 1.93 | 1137.98 ± 6.98 | 3600.31 ± 6.32 | 96.14 ± 1.17 |
| | Batch 4 | 47.6 ± 0.63 | 192.75 ± 1.16 | 109.89 ± 1.04 | 171.23 ± 0.85 | 3366.86 ± 3.24 | 929.49 ± 2.06 | 3307.86 ± 4.75 | 89.9 ± 1.03 |
| | Batch 5 | 66.24 ± 0.89 | 169.21 ± 0.62 | 103.64 ± 0.7 | 167.75 ± 0.02 | 2943.54 ± 3.53 | 1282.9 ± 5.34 | 3403.56 ± 8.75 | 69.71 ± 0.79 |
| | Batch 6 | 70 ± 0.78 | 184.11 ± 0.86 | 103.48 ± 0.96 | 162.37 ± 1.01 | 2113.04 ± 5.15 | 643.58 ± 3.75 | 3002.94 ± 4.11 | 103.77 ± 2.81 |

Comparative Example 1 Fuke Qianjin Capsules

The cream in which the contents of Z-ligustilide, Z-3-butylidenephthalide, genistin, jatrorrhizine, palmatine and berberine in Embodiment 1 were not within the range required by Embodiment 1 was selected and directly performed with spray drying, and then pelletizing, canning to obtain the Fuke Qianjin Capsules. According to the 2015 edition of the Pharmacopoeia of the People's Republic of China, the content of each Fuke Qianjin Capsule was 0.4 g. The same method was used for HPLC detection for each batch of the Fuke Qianjin Capsules.

The detection conditions and methods are the same as Embodiment 1, and the detection results are shown in Table 2.

TABLE 2

Contents of eight ingredients in Fuke Qianjin Capsules prepared in Comparative Example 1 (μg/capsule)

| | Batch 1 | Batch 2 | Batch 3 | Batch 4 |
|---|---|---|---|---|
| Genistin/mg | 24.35 ± 0.46 | 21.33 ± 0.25 | 24.21 ± 0.23 | 18.08 ± 1.11 |
| Jatrorrhizine/mg | 71.56 ± 0.16 | 76.35 ± 1.68 | 67.84 ± 1.22 | 58.26 ± 2.63 |
| Palmatine/mg | 55.33 ± 1.23 | 51.32 ± 0.26 | 48.76 ± 0.25 | 59.03 ± 1.07 |
| Berberine/mg | 75.10 ± 0.22 | 54.10 ± 0.42 | 73.26 ± 0.32 | 69.16 ± 0.56 |
| Andrographolide/mg | 1380.26 ± 10.38 | 1131.26 ± 7.18 | 1065.56 ± 5.62 | 1166.61 ± 14.02 |
| Dehydroandrographolide/mg | 568.72 ± 8.85 | 651.04 ± 0.54 | 718.24 ± 0.32 | 562.58 ± 10.22 |
| Z-ligustilide/mg | 1684.02 ± 2.35 | 1700.34 ± 2.05 | 1573.36 ± 5.16 | 1710.25 ± 1.68 |
| Z-3-butylidenephthalide/mg | 23.31 ± 0.24 | 18.35 ± 1.20 | 28.15 ± 1.16 | 25.21 ± 1.67 |

It can be seen from Table 2 that in the Fuke Qianjin Capsules prepared according to the existing method, except that the content of andrographolide and dehydroandrographolide meets the requirements of the Pharmacopoeia, the contents of other active ingredients vary greatly between batches, which can easily lead to instability of drug efficacy.

Embodiment 3 In Vitro Efficacy Test

Medicines or materials used: croton oil, provided by Nanjing Institute of Dermatology; carrageenan, produced by Wako Pure Chemical Industries, Ltd.; nutrient broth medium, product of Guangdong Huankai Microbial Technology Co., Ltd.; and mould medium, provided by China National Institute for the Control of Pharmaceutical and Biological Products.

The Fuke Qianjin Capsules prepared by Embodiment 1 (batch 1 and batch 6) and Comparative Example 1 (batch 1) were used as samples. Kunming mice of clean grade and SD rats used were provided by the Hunan Institute for Drug Control; *Escherichia coli* ATCC25922, *Staphylococcus aureus* ATCC25923, beta hemolytic *Streptococcus* ATCC32172 were all provided by the Provincial Health and Epidemic Prevention Station, *Candida albicans*, isolated from the clinic, was provided by the Bacteria Room of the Clinical Laboratory Department of the Third Affiliated Hospital of Hunan Medical University.

1) In Vitro Antibacterial Test on Standard Bacteria

The results are shown in Table 3 to Table 5.

TABLE 3

Antibacterial test results of Fuke Qianjin Capsules of batch 1 in Embodiment 1 (liquid test tube method)

| Bacteria | Bacterial concentration (GFu/mL) | Drug concentration (%) | | | | | Blank control |
|---|---|---|---|---|---|---|---|
| | | 50.0 | 25.0 | 12.5 | 6.25 | 3.13 | |
| *Escherichia coli* | $10^6$ | == | == | == | + | ++ | +++ |
| *Staphylococcus aureus* | $10^6$ | == | == | == | == | + | +++ |
| Beta hemolytic *streptococcus* | $10^6$ | == | == | == | + | ++ | +++ |
| *Candida albicans* | $10^6$ | == | == | == | + | ++ | +++ |

TABLE 4

Antibacterial test results of Fuke Qianjin Capsules of batch 6 in Embodiment 1 (liquid test tube method)

| Bacteria | Bacterial concentration (GFu/mL) | Drug concentration (%) | | | | | Blank control |
|---|---|---|---|---|---|---|---|
| | | 50.0 | 25.0 | 12.5 | 6.25 | 3.13 | |
| *Escherichia coli* | $10^6$ | == | == | == | + | ++ | +++ |
| *Staphylococcus aureus* | $10^6$ | == | == | == | == | + | +++ |
| Beta hemolytic *streptococcus* | $10^6$ | == | == | == | + | ++ | +++ |
| *Candida albicans* | $10^6$ | == | == | == | + | ++ | +++ |

TABLE 5

Antibacterial test results of Fuke Qianjin Capsules of batch 1 in Comparative Example 1 (liquid test tube method).

| Bacteria | Bacterial concentration (GFu/mL) | Drug concentration (%) | | | | | Blank control |
|---|---|---|---|---|---|---|---|
| | | 50.0 | 25.0 | 12.5 | 6.25 | 3.13 | |
| *Escherichia coli* | $10^6$ | == | == | == | + | ++ | +++ |
| *Staphylococcus aureus* | $10^6$ | == | == | == | == | + | +++ |
| Beta hemolytic *streptococcus* | $10^6$ | == | == | == | + | ++ | +++ |
| *Candida albicans* | $10^6$ | == | == | == | + | ++ | +++ |

== indicates that there is no bacterial growth in two repeated experiments, and +, ++, +++ indicate the degree of cell growth, respectively.

The experimental results of Table 3 to Table 5 show that: the Fuke Qianjin Capsules of Embodiment 1 and Comparative Example 1 have minimum inhibitory concentrations of 12.5, 6.25, 12.5, 12.5 for *Escherichia coli*, *Staphylococcus aureus*, beta hemolytic *Streptococcus* and *Candida albicans*, respectively, and the inhibitory concentrations of the two are the same.

2) In Vitro Antibacterial Experiment on Clinically Isolated Pathogenic Bacteria

*Escherichia coli*, *Staphylococcus aureus*, beta hemolytic *Streptococcus*, and *Candida albicans* were all isolated from clinical patients and identified by bacteriology, provided by the Bacteria Room of the Clinical Laboratory Department of the Third Affiliated Hospital of Hunan Medical University.

The results are shown in Table 6 to Table 8.

TABLE 6

Antibacterial test results of Fuke Qianjin Capsules of batch 1 of Embodiment 1 on clinical isolation (liquid test tube method)

| Bacterial strain | Plant number (plant) | Bacterial concentration (GFu/mL) | Minimal inhibitory concentration (%) |
|---|---|---|---|
| *Escherichia coli* | 32 | $10^5$~$10^6$ | 50.0~25.0 |
| *Staphylococcus aureus* | 23 | $10^5$~$10^6$ | 12.5~3.13 |
| Beta hemolytic *streptococcus* | 20 | $10^5$~$10^6$ | 50.0~25.0 |
| *Candida albicans* | 27 | $10^5$~$10^6$ | 12.5~3.13 |

TABLE 7

Antibacterial test results of Fuke Qianjin Capsules of batch 6 of Embodiment 1 on clinical isolation (liquid test tube method)

| Bacterial strain | Plant number (plant) | Bacterial concentration (GFu/mL) | Minimal inhibitory concentration (%) |
|---|---|---|---|
| *Escherichia coli* | 32 | $10^5$~$10^6$ | 50.0~25.0 |
| *Staphylococcus aureus* | 23 | $10^5$~$10^6$ | 12.5~3.13 |
| Beta hemolytic *streptococcus* | 20 | $10^5$~$10^6$ | 50.0~25.0 |
| *Candida albicans* | 27 | $10^5$~$10^6$ | 12.5~3.13 |

TABLE 8

Antibacterial test results of Fuke Qianjin Capsules
of batch 1 of Comparative Example 1 on clinical
isolation (liquid test tube method)

| Bacterial strain | Plant number (plant) | Bacterial concentration (GFu/mL) | Minimal inhibitory concentration (%) |
|---|---|---|---|
| Escherichia coli | 32 | $10^5$~$10^6$ | 50.0~25.0 |
| Staphylococcus aureus | 23 | $10^5$~$10^6$ | 12.5~3.13 |
| Beta hemolytic streptococcus | 20 | $10^5$~$10^6$ | 50.0~25.0 |
| Candida albicans | 27 | $10^5$~$10^6$ | 12.5~3.13 |

The experimental results of Table 6 to Table 8 show that the Fuke Qianjin Capsules prepared by Embodiment 1 and Comparative Example 1 have the same inhibitory effect on the four clinically isolated bacteria, and the effect is consistent.

3) Antibacterial Experiment In Vivo

Protective effect on *Escherichia coli*-infected mice: 150 Kunming mice, both male and female, weighing 20-22 g, were divided into 15 groups (n=10), five groups were used for the Fuke Qianjin Capsules of batch 1 of Embodiment 1, five groups were used for the Fuke Qianjin Capsules of batch 6 of Embodiment 1, and five groups were used for the Fuke Qianjin Capsules of batch 1 of Comparative Example 1, and the doses were 17.3, 24.7, 35.3, 50.4 and 72.0 g crude drug/kg.

Volume of intragastric administration was 0.5 mL/20 g, and each mouse in each group was injected with 0.5 mL of *Escherichia coli* (106 FGu/mL) decoction culture solution one hour after the administration. At 12 hours and 24 hours after the mice were infected with the bacteria, the mice were administered twice, and then observed for seven days, and the number of animal deaths was recorded. The peak of animal deaths was between 24 hours and 48 hours.

TABLE 9

Protective effect of Fuke Qianjin Capsules
on *Escherichia coli*-infected mice

| Group | Dosage (g/kg) | Animal numbers | Death count | Protection rate (%) |
|---|---|---|---|---|
| Fuke Qianjin Capsules (batch 1 of Embodiment) | 72.0 | 10 | 4 | 60 |
| | 50.4 | 10 | 6 | 40 |
| | 35.3 | 10 | 8 | 20 |
| | 24.7 | 10 | 9 | 10 |
| | 17.3 | 10 | 0 | 0 |
| Fuke Qianjin Capsules (batch 6 of Embodiment) | 72.0 | 10 | 4 | 60 |
| | 50.4 | 10 | 6 | 40 |
| | 35.3 | 10 | 8 | 20 |
| | 24.7 | 10 | 9 | 10 |
| | 17.3 | 10 | 0 | 0 |
| Fuke Qianjin Capsules (batch 1 of Comparative Example 1) | 72.0 | 10 | 4 | 60 |
| | 50.4 | 10 | 6 | 40 |
| | 35.3 | 10 | 8 | 20 |
| | 24.7 | 10 | 9 | 10 |
| | 17.3 | 10 | 0 | 0 |

The experimental results in Table 9 show that the Fuke Qianjin Capsules prepared by Embodiment 1 and Comparative Example 1 have a certain protective effect on *Escherichia coli*-infected mice in the high-dose group.

4) Anti-Inflammatory Effect (Influence on Croton Oil-Induced Swelling in Mice)

Preparation of drugs to be used: the ready-to-use contents of Fuke Qianjin Capsules were taken and prepared into suspensions of different concentrations with distilled water for mice. Intragastric administration was performed once a day, and the liquid for intragastric administration was used it right after it was prepared.

100 mice, male, weighing 24-26 g, were equally divided into 10 groups (n=10), and were given different concentrations of liquid medicine by intragastric administration, and the control group was given with equal volume of distilled water by intragastric administration once a day for 7 days, 1 hour after the last administration was performed, the right ear of each mouse was applied with 0.1 mL of 2% croton oil (2% croton oil, 20% anhydrous ethanol, 5% distilled water and 73% diethyl ether), and no treatment was applied on the left ear of all mice. On the 7th day, 4 hours after the last administration, the mice were sacrificed by cervical dislocation, the ears were cut off, punched and weighed, and the swelling degree of each group of mice was calculated.

TABLE 10

Influence of Fuke Qianjin Capsules on croton oil-induced
ear swelling in mice (X ± SD, n = 10)

| Group | Dosage (g/kg) | Weight of right ear (mg) | Weight of left ear (mg) | Swelling degree (mg) | Inhibition rate (%) |
|---|---|---|---|---|---|
| Control group | 16 g/kg distilled water | 30.3 ± 3.7 | 9.5 ± 1.0 | 20.8 ± 4.1 | — |
| Fuke Qianjin Capsules (batch 6 of Embodiment 1) | 16 | 17.4 ± 1.7 | 9.5 ± 1.2 | 7.9 ± 0.8*** | 62.02% |
| | 8 | 18.7 ± 2.4 | 9.2 ± 1.1 | 9.5 ± 0.4*** | 54.3% |
| | 4 | 21 ± 1.1 | 9.1 ± 1.2 | 11.9 ± 0.6** | 42.8% |
| Fuke Qianjin Capsules (batch 1 of Embodiment 1) | 16 | 20.8 ± 2.1 | 9.7 ± 1.0 | 11.1 ± 0.7** | 46.6% |
| | 8 | 21.8 ± 4.5 | 9.3 ± 1.0 | 12.5 ± 0.7** | 39.9% |
| | 4 | 23 ± 2.3 | 8.9 ± 1.4 | 14.1 ± 0.6* | 32.2% |
| Fuke Qianjin Capsules (batch 1 of Comparative Example 1) | 16 | 21.2 ± 2.1 | 9.3 ± 1.1 | 11.9 ± 0.5** | 42.8% |
| | 8 | 22.6 ± 1.7 | 9.4 ± 1.2 | 13.2 ± 0.7** | 36.5% |
| | 4 | 23.3 ± 1.1 | 9.1 ± 1.0 | 14.2 ± 0.8* | 31.7% |

Compared with the control group,
*$P > 0.05$,
**$P < 0.05$,
***$P < 0.01$

The results in Table 10 show that: compared with the control group, the Fuke Qianjin Capsules prepared by Embodiment 1 and Comparative Example 1 can both significantly inhibit croton oil-induced ear swelling in mice; however, the inhibition effect of the two batches in Embodiment 1 is significantly better than the Fuke Qianjin Capsules of Comparative Example 1.

5) Influence on Carrageenan-Induced Footpad Swelling in Rats

70 SD rats, males, were divided into seven groups (n=10), and they were given different concentrations of liquid medicine by intragastric administration, and the control group was given with the same volume of distilled water by intragastric administration, once a day for seven days, 1 hour after the last administration was performed, 0.1 mL of carrageenan was injected into the bottom of the right pedal of each rat to cause inflammation. 2 hours after the inflammation, it is administered again. In addition to measuring the size of the normal pedal before the inflammation, the size of pedal was measured every 1 hour after the inflammation for a total of 6 times, and the swelling degree was calculated.

TABLE 12

Influence of Fuke Qianjin Capsules on painful mice induced by acetic acid (X ± SD, n = 10)

| Group | Dosage (g/kg) | Writhing times (times) | Inhibition rate (%) |
|---|---|---|---|
| Control group | 18.2 g/kg distilled water | 22.4 ± 1.8 | — |
| Fuke Qianjin Capsules (batch 6 of Embodiment) | 18.2 | 6.8 ± 1.1*** | 69.6% |
|  | 9.1 | 9.2 ± 1.5*** | 58.9% |
|  | 3.6 | 10.8 ± 1.2*** | 51.8% |
| Fuke Qianjin Capsules (batch 1 of Embodiment) | 18.2 | 9.2 ± 1.2*** | 58.9% |
|  | 9.1 | 10.9 ± 1.3*** | 51.3% |
|  | 3.6 | 13.1 ± 1.7** | 41.5% |
| Fuke Qianjin Capsules (batch 1 of Comparative Example) | 18.2 | 9.6 ± 1.8*** | 57.1% |
|  | 9.1 | 11.0 ± 1.6*** | 50.9% |
|  | 3.6 | 13.4 ± 1.5** | 40.2% |

Compared with the control group,
**$P < 0.05$,
***$P < 0.01$

TABLE 11

Influence of Fuke Qianjin Capsules on carrageenan-induced footpad swelling in rats (X ± cm, n = 10)

| Group | Dosage (g/kg) | Pedal size before experiment (cm) | Swelling degree after inflammation (cm) | | | | | |
|---|---|---|---|---|---|---|---|---|
| | | | 1 hour | 2 hours | 3 hours | 4 hours | 5 hours | 6 hours |
| Control group | 10.08 g/kg distilled water | 2.4 ± 0.3 | 0.45 ± 0.1 | 0.73 ± 0.1 | 0.96 ± 0.1 | 0.80 ± 0.3 | 0.62 ± 0.1 | 0.52 ± 0.2 |
| Fuke Qianjin Capsules (batch 6 of Embodiment) | 10.08 | 2.5 ± 0.1* | 0.22 ± 0.1** | 0.30 ± 0.2** | 0.47 ± 0.1*** | 0.44 ± 0.3*** | 0.35 ± 0.1** | 0.23 ± 0.1** |
|  | 5.04 | 2.6 ± 0.1 | 0.30 ± 0.1* | 0.38 ± 0.2* | 0.53 ± 0.1** | 0.50 ± 0.3** | 0.41 ± 0.1* | 0.29 ± 0.1** |
|  | 2.52 | 2.7 ± 0.1 | 0.35 ± 0.1* | 0.42 ± 0.2* | 0.59 ± 0.1** | 0.56 ± 0.3* | 0.43 ± 0.1* | 0.32 ± 0.1** |
| Fuke Qianjin Capsules (batch 1 of Embodiment) | 10.08 | 2.5 ± 0.1 | 0.31 ± 0.1* | 0.37 ± 0.2* | 0.66 ± 0.1** | 0.58 ± 0.3* | 0.40 ± 0.1* | 0.3 ± 0.1** |
|  | 5.04 | 2.7 ± 0.1 | 0.34 ± 0.1* | 0.43 ± 0.2* | 0.70 ± 0.1* | 0.60 ± 0.3* | 0.41 ± 0.1* | 0.35 ± 0.1* |
|  | 2.52 | 2.7 ± 0.1 | 0.40 ± 0.1 | 0.49 ± 0.2 | 0.75 ± 0.1* | 0.67 ± 0.3 | 0.44 ± 0.1* | 0.36 ± 0.1* |
| Fuke Qianjin Capsules (batch 1 of Comparative Example 1) | 10.08 | 2.4 ± 0.1 | 0.31 ± 0.1* | 0.4 ± 0.2* | 0.67 ± 0.1** | 0.6 ± 0.3* | 0.4 ± 0.1* | 0.3 ± 0.1** |
|  | 5.04 | 2.6 ± 0.1 | 0.34 ± 0.1* | 0.43 ± 0.2* | 0.71 ± 0.1* | 0.62 ± 0.3* | 0.41 ± 0.1* | 0.35 ± 0.1* |
|  | 2.52 | 2.8 ± 0.1 | 0.41 ± 0.1 | 0.52 ± 0.2 | 0.79 ± 0.1* | 0.65 ± 0.3* | 0.44 ± 0.1* | 0.38 ± 0.1* |

Compared with the control group, *$P > 0.05$, $P < 0.05$, *$P < 0.01$

The results in Table 11 show that: compared with the control group, the Fuke Qianjin Capsules prepared by Embodiment 1 and Comparative Example 1 can significantly inhibit the carrageenan-induced footpad swelling in rats; however, the two batches of the Fuke Qianjin Capsules in Embodiment 1 have better inhibitory effects on the carrageenan-induced footpad swelling in rats than the Fuke Qianjin Capsules of Comparative Example 1, especially in the 3-4 hours period after the administration.

6) Influence on Induced Painful Mice Induced by Acetic Acid 100 mice, half male and half male, weighing 20-22 g, were randomly divided into 10 groups (n=10), and they were given different concentrations of liquid medicine by intragastric administration, and the control group was given with the same volume of distilled water by intragastric administration, one hour after the administration, each mouse was injected with 0.2 mL of 0.6% acetic acid. 5 minutes after the injection, the recording was started, and the number of mouse writhing times in 10 minutes was recorded.

The results in Table 12 show that: compared with the control group, the Fuke Qianjin Capsules prepared by Embodiment 1 and Comparative Example 1 can significantly reduce the number of writhing times of painful mice induced by acetic acid; however, the effect of the two batches of the Fuke Qianjin Capsules in Embodiment 1 on the pain induced by acetic acid is significantly better than the Fuke Qianjin Capsules of Comparative Example 1.

7) Influence on Pain Threshold of Painful Mice Induced by Hot Plate Test

Pain threshold of a mouse was measured according to the following method: the mouse was placed on a 55±0.5° C. hot plate at a room temperature of 20±1° C., and the time from touching the hot plate to licking the rear foot was the pain threshold.

Then 100 female mice with a pain threshold of less than 30 seconds, weighing 20-22 g, were divided into 10 groups (n=10), and they were given by one-time intragastric administration according to the dose of painful mice induced by acetic acid, and according to the above measuring method, the pain thresholds were measured at 55±0.5° C. before administration and 30, 60 and 90 minutes after administration, and the results are shown in Table 13.

TABLE 13

Influence of Fuke Qianjin Capsules on pain threshold of painful mice induced by hot plate test (X ± SD, n = 10)

| | | | 30 minutes | | | 60 minutes | | | 90 minutes | |
|---|---|---|---|---|---|---|---|---|---|---|
| Group | Dosage (g/kg) | Pain threshold before administration (s) | Pain threshold after administration (s) | Percentage increase in pain threshold/% | Pain threshold after administration (s) | Percentage increase in pain threshold/% | Pain threshold after administration (s) | Percentage increase in pain threshold/% |
| Control group | 18.2 g/kg water | 18.8 ± 5.3 | 25 ± 5.5 | 32.9 | 29.1 ± 4.5 | 53.2 | 27.3 ± 7.5 | 45.2 |
| Fuke Qianjin Capsules (batch 6 of Embodiment) | 18.2 | 18.1 ± 5.1 | 55.8 ± 6.3*** | 208.3 | 51.8 ± 7.2*** | 186.2 | 49 ± 3.5*** | 170.7 |
| | 9.1 | 18.7 ± 5.4 | 52.2 ± 6.1*** | 179.1 | 48.4 ± 3.5*** | 158.8 | 46.9 ± 4.5* ** | 150.8 |
| | 3.6 | 18.0 ± 4.2 | 46.2 ± 5.5** | 155.7 | 43.4 ± 4.3** | 141.1 | 40.8 ± 4.8** | 126.7 |
| Fuke Qianjin Capsules (batch 1 of Embodiment) | 18.2 | 18.1 ± 3.5 | 52.1 ± 5.1*** | 187.8 | 48.4 ± 5.7*** | 167.4 | 45.6 ± 6.5*** | 151.9 |
| | 9.1 | 18.2 ± 5.7 | 48.2 ± 6.1*** | 164.8 | 45 ± 6.2*** | 147.3 | 42.1 ± 4.7** | 131.3 |
| | 3.6 | 18.3 ± 4.8 | 43.1 ± 4.5** | 135.5 | 42.5 ± 5.2** | 132.2 | 40.4 ± 5.5** | 120.8 |
| Fuke Qianjin Capsules (batch 1 of Comparative Example 1) | 18.2 | 18.4 ± 5.7 | 51.2 ± 5.3*** | 178.3 | 48.4 ± 5.2*** | 163.0 | 44.1 ± 4.5*** | 139.6 |
| | 9.1 | 18.9 ± 6.1 | 49.3 ± 5.1*** | 160.8 | 45.2 ± 4.5*** | 139.1 | 42.9 ± 3.5** | 126.9 |
| | 3.6 | 18.0 ± 6.0 | 41.3 ± 4.5** | 129.4 | 40 ± 5.3** | 122.2 | 37.8 ± 3.8** | 110.0 |

Compared with the control group, P < 0.05, *P < 0.01

The results in Table 13 show that compared with the control group, the Fuke Qianjin Capsules of Embodiment 1 and Comparative Example 1 can significantly increase the pain threshold of painful mice induced by hot plate excitement; however, the percentage increase in pain threshold of painful mice induced by hot plate excitement of the two batches of Fuke Qianjin Capsules in Embodiment 1 is significantly higher than the Fuke Qianjin Capsules of Comparative Example 1.

8) Influence on Hemorrhagic Blood Deficiency Mice 110 mice, both male and female, weighing 20-22 g, were divided into 11 groups (n=10), First, blood was taken to measure normal values RBC (red blood cell) and HB (haemoglobin) of the mice, then, except for the normal control group, each mouse in the other groups was bled 0.5 mL from the orbital venous plexus, 24 hours later, blood was taken to measure the RBC and HB values of the mice, and then different doses of medicine were given by intragastric administration, once a day for seven days, 24 hours after the last administration, blood was taken from the orbital venous plexus of the mice to measure the RBC and HB values, and the results are shown in Table 14.

TABLE 14

Influence of Fuke Qianjin Capsules on hemorrhagic blood deficiency mice (X ± SD, n = 10)

| | | RBC(×10¹²/L) | | | HB(g/L) | | |
|---|---|---|---|---|---|---|---|
| Group | Dosage (g/kg) | Before blood loss | After blood loss | After treatment | Before blood loss | After blood loss | After treatment |
| Normal control group | Equal volume of water | 6.76 ± 0.52 | 6.25 ± 0.41 | 6.54 ± 0.37 | 136.0 ± 2.6 | 124.4 ± 2.4 | 129.2 ± 3.1 |
| Model control group | Equal volume of water | 6.81 ± 0.46 | 3.51 ± 0.27 | 5.01 ± 0.31 | 135.0 ± 42 | 77.8 ± 3.1 | 97.4 ± 3.5 |
| Fuke Qianjin Capsules (batch 6 of Embodiment) | 18.2 | 6.79 ± 0.34 | 3.67 ± 0.36 | 5.71 ± 0.18** | 131.4 ± 3.2 | 77.01 ± 3.2 | 109.4 ± 2.3** |
| | 9.1 | 7.01 ± 0.42 | 3.62 ± 0.46 | 5.48 ± 0.25* | 131.6 ± 4.1 | 73.5 ± 2.2 | 101.6 ± 2.7* |
| | 3.6 | 7.04 ± 0.26 | 3.55 ± 0.19 | 5.09 ± 0.21 | 135.4 ± 2.7 | 74.8 ± 1.8 | 97.4 ± 2.1 |
| Fuke Qianjin Capsules (batch 1 of Embodiment) | 18.2 | 7.04 ± 0.28 | 3.86 ± 0.24 | 5.71 ± 0.37** | 133.5 ± 1.6 | 78.5 ± 1.8 | 108.1 ± 2.2* |
| | 9.1 | 7.03 ± 0.54 | 3.74 ± 0.22 | 5.38 ± 0.28* | 132.4 ± 2.7 | 78.6 ± 2.5 | 103.7 ± 2.1* |
| | 3.6 | 7.04 ± 2.1 | 3.84 ± 0.34 | 5.35 ± 0.27 | 138.4 ± 3.1 | 76.6 ± 2.2 | 98.9 ± 3.4 |
| Fuke Qianjin Capsules (batch 1 of Comparative Example) | 18.2 | 7.02 ± 0.26 | 3.80 ± 0.24 | 5.58 ± 0.24* | 133.7 ± 3.4 | 77.2 ± 1.5 | 106.5 ± 2.0* |
| | 9.1 | 7.03 ± 0.23 | 3.50 ± 0.44 | 5.11 ± 0.24 | 130.4 ± 2.8 | 77.9 ± 1.7 | 103.5 ± 2.8* |
| | 3.6 | 7.01 ± 0.57 | 3.72 ± 0.27 | 5.24 ± 0.25 | 132.8 ± 4.2 | 76.4 ± 2.6 | 97.8 ± 3.1 |

Compared with the model group, *P < 0.05, **P < 0.01

The results in Table 14 show that, compared with the control group, the fuke qianjin ta capsules of Embodiment 1 and Comparative Example 1 both have a significant blood-enriching effect on hemorrhagic blood deficiency mice; however, the two batches of Fuke Qianjin Capsules in Embodiment 1 have a significantly higher blood-enriching effect on hemorrhagic blood deficiency mice than the Fuke Qianjin Capsules of Comparative Example.

Throughout the above experimental results, it can be seen that the Fuke Qianjin Capsules of Embodiment 1 and Comparative Example 1 have the same in vitro minimal inhibitory concentration for *Escherichia coli, Staphylococcus aureus*, beta hemolytic *Streptococcus* and *Candida albicans*, as well as the minimal inhibitory concentration of the above four clinically isolated bacteria.

However, in mice in vivo experiments, the Fuke Qianjin Capsules of the two batches in Embodiment 1 and in Comparative Example 1 can significantly inhibit croton oil-induced ear swelling in mice and carrageenan-induced footpad swelling in rats; reduce the number of writhing times in mice induced by acetic acid, and increase the pain threshold of painful mice induced by hot plate test; and can also have a significant blood-enriching effect on hemorrhagic blood deficiency mice; however, The above-mentioned effects of the Fuke Qianjin Capsules prepared in the two batches in Embodiment 1 have a certain degree of improvement compared with the Fuke Qianjin Capsules of Comparative Example 1, and the effects are better than the Fuke Qianjin Capsules of Comparative Example 1.

Embodiment 4 Clinical Results

In order to compare whether there is a difference between the Fuke Qianjin Capsules that the present invention controls the content of multiple active ingredients and the Fuke Qianjin Capsules prepared by the original method (i.e., Comparative Example 1), a clinical trial was conducted. In accordance with the requirements of relevant new drug research, each test site has formulated clinical research principles, established diagnostic criteria, inclusion criteria, and rejection criteria, and used this as a guideline to collect observation cases. At the same time, method of taking medicine was followed in the instructions attached to the medicine during use, the medicine was started taking when seeing a doctor, 7 days as a course of treatment, two consecutive courses of treatment, and clinical symptoms and changes in symptoms were collected according to the planned clinical observation form.

Table 15 shows the clinical changes of 240 patients with chronic pelvic inflammatory disease in the Second Affiliated Hospital of Hunan University of Traditional Chinese Medicine, Hunan Academy of Traditional Chinese Medicine, and the First Affiliated Hospital of Hunan Medical University after taking qianjin capsules for two courses, divided into 3 groups, 80 patients in each group. The specific results are shown in Table 15.

TABLE 15

Patients with chronic pelvic inflammatory disease getter better after treatment and percentage table

| | Symptom name | Low fever | Fatigue | Lack of energy | Whole body discomfort | Insomnia | Hypogastralgia | Soreness of waist | Irregular menstruation | Increased leucorrhea |
|---|---|---|---|---|---|---|---|---|---|---|
| Fuke Qianjin Capsules (batch 6 of Embodiment) | Number of people before treatment | 10 | 40 | 32 | 22 | 15 | 55 | 49 | 24 | 48 |
| | Number of people getting better | 10 | 34 | 30 | 19 | 12 | 52 | 44 | 23 | 47 |
| | Rate of getting better % | 100 | 85 | 93.8 | 86.4 | 80.0 | 94.5 | 89.8 | 95.8 | 97.9 |
| Fuke Qianjin Capsules (batch 1 of Embodiment) | Number of people before treatment | 9 | 36 | 33 | 27 | 15 | 52 | 45 | 21 | 50 |
| | Number of people getting better | 9 | 30 | 28 | 22 | 10 | 47 | 35 | 18 | 46 |
| | Rate of getting better % | 100 | 83.3 | 84.8 | 81.5 | 66.7 | 90.4 | 77.8 | 85.7 | 92.0 |
| Fuke Qianjin Capsules (batch 1 of Comparative Example) | Number of people before treatment | 11 | 38 | 33 | 26 | 16 | 55 | 47 | 20 | 50 |
| | Number of people getting better | 10 | 31 | 27 | 21 | 10 | 48 | 36 | 17 | 45 |
| | Rate of getting better % | 90 | 81.6 | 81.8 | 80.8 | 62.5 | 87.3 | 76.6 | 85.0 | 90.0 |

The effect statistics of 240 patients with adnexitis taking Fuke Qianjin Capsules were listed in Tables 16 to 18, wherein Table 16 is the examination status of the 240 patients with adnexitis, Table 17 is the efficacy statistics, and Table 18 is the change in symptoms before and after taking the Fuke Qianjin Capsules.

TABLE 16

Examination status of patients with adnexitis

| Site | Number of cases | Obvious tenderness | General tenderness | Light tenderness |
|---|---|---|---|---|
| Unilateral adnexitis | 99 | 30 | 53 | 16 |
| Bilateral adnexitis | 141 | 63 | 60 | 18 |
| Total | 240 | 93 | 113 | 34 |

TABLE 17

Efficacy of Fuke Qianjin Capsules in patients with annexitis

| | Bilateral adnexitis | | | Unilateral adnexitis | | | Overal efficacy | | |
|---|---|---|---|---|---|---|---|---|---|
| Site Efficacy | Markedly effective | Getting better | Noneffective | Markedly effective | Getting better | Noneffective | Markedly effective | Getting better | Noneffective |
| Number of cases (batch 6 of Embodiment 1) | 24 | 21 | 2 | 21 | 11 | 1 | 45 | 32 | 3 |
| Number of cases (batch 1 of Embodiment 1) | 22 | 22 | 3 | 19 | 12 | 2 | 41 | 34 | 5 |
| Number of cases (batch 1 of Comparative Example) | 21 | 23 | 3 | 19 | 12 | 2 | 40 | 35 | 5 |

TABLE 18

Changes in symptoms of patients with adnexitis before and after taking Fuke Qianjin Capsules

| | | Soreness of waist and tenesmus | hypogastralgia | Lumbago | Increased leucorrhea | dysmenorrhea |
|---|---|---|---|---|---|---|
| Qianjin capsules (batch 6 of Embodiment) | Number of people before treatment | 58 | 55 | 53 | 44 | 47 |
| | Significantly reduced | 51 | 51 | 51 | 43 | 39 |
| | Getting better | 6 | 4 | 2 | 1 | 6 |
| | Noneffective | 1 | 0 | 0 | 0 | 2 |
| | Rate of getter better/% | 98.3 | 100 | 100 | 100 | 95.7 |
| Qianjin capsules (batch 1 of Embodiment) | Number of people before treatment | 59 | 51 | 53 | 40 | 45 |
| | Significantly reduced | 49 | 49 | 49 | 37 | 37 |
| | Getting better | 8 | 2 | 3 | 2 | 6 |
| | Noneffective | 2 | 0 | 1 | 1 | 2 |
| | Rate of getter better/% | 96.6 | 100 | 98.1 | 97.4 | 95.6 |
| Qianjin capsules (batch 1 of Comparative Example) | Number of people before treatment | 60 | 52 | 52 | 41 | 44 |
| | Significantly reduced | 50 | 48 | 48 | 34 | 32 |
| | Getting better | 7 | 3 | 3 | 5 | 9 |
| | Noneffective | 3 | 1 | 1 | 2 | 3 |
| | Rate of getter better/% | 95 | 98.1 | 98.1 | 95.1 | 90.6 |

It can be seen from Tables 15 to 18 that the Fuke Qianjin Capsules of the present invention is better than the Fuke Qianjin Capsules of Comparative Example 1 in the treatment of chronic pelvic inflammatory disease and adnexitis, wherein the effect of batch 6 of Embodiment is better than that of batch 1, and the effect of batch 1 of Embodiment is better than that of Comparative Example. It reflects that in addition to controlling the contents of Z-ligustilide, Z-3-butylidenephthalide, andrographolide and dehydroandrographolide, it also controls the contents of genistin, jatrorrhizine, palmatine and berberine within a standard range, and the therapeutic effect can be further improved.

Embodiment 5 Clinical Results of Endometritis

According to the good results shown in the treatment of chronic pelvic inflammatory disease, we also compared the efficacy of the treatment of endometritis. Specifically, 608 patients with endometritis were selected as study subjects, aged between 30 and 40 years old, and the treatment plan was to give antibiotics combined with progesterone for treatment. 0.5 g of metronidazole was added into 250 mL of 0.9% sodium chloride solution, intravenously dripped, once every 8 hours, medroxyprogesterone was taken 4 mg/time, 2 times a day for 14 days after the end of menstruation on the 3rd day, and this is used as a blank control group. The observation group was given the Fuke Qianjin Capsules of Embodiment 1 (3 batches) and Embodiment 2 (3 batches) on the basis of the blank control group, and the control group was given the Fuke Qianjin Capsules prepared in Comparative Example 1 (3 batches) on the basis of the blank control group. The treatment results are shown in Tables 19 to 21.

Evaluation Criteria:
Markedly effective: the clinical symptoms disappeared, the menstruation returned to normal, and the ultrasound examination showed that the inflammation disappeared;
Effective: clinical symptoms got better, and the ultrasound examination showed that the inflammation got better and endometrium was thickened;
Noneffective: no improvement as described above.

TABLE 19

Comparison of clinical efficacy

| Batch (number of cases) | | Markedly effective | Effective | Non-effective | Markedly effective rate/% | Effective rate/% |
|---|---|---|---|---|---|---|
| Embodiment 1 (183 cases) | Batch 1 (62 cases) | 38 | 18 | 6 | 61.29 | 90.32 |
| | Batch 3 (60 cases) | 37 | 17 | 6 | 61.67 | 90.0 |
| | Batch 6 (61 cases) | 38 | 18 | 5 | 62.30 | 91.8 |
| Embodiment 2 (184 cases) | Batch 1 (60 cases) | 41 | 14 | 5 | 68.33 | 91.67 |
| | Batch 3 (62 cases) | 42 | 15 | 5 | 67.74 | 91.94 |
| | Batch 5 (62 cases) | 42 | 16 | 4 | 67.74 | 93.55 |
| Comparative Example (179 cases) | Batch 1 (60 cases) | 35 | 18 | 7 | 58.33 | 88.33 |
| | Batch 2 (59 cases) | 34 | 17 | 8 | 57.63 | 86.44 |
| | Batch 3 (60 cases) | 35 | 18 | 7 | 58.33 | 88.33 |
| Blank control (62 cases) | | 27 | 22 | 13 | 43.55 | 79.03 |

TABLE 20

Comparison of menstruation recovery

| Batch (number of cases) | | Menstrual blood volume returned to normal (proportion %) | Menstrual period returned to normal (proportion %) | Irregular vaginal bleeding (proportion %) |
|---|---|---|---|---|
| Embodiment 1 (183 cases) | Batch 1 (62 cases) | 54 (87.1%) | 55 (88.71%) | 3 (4.84%) |
| | Batch 3 (60 cases) | 53 (88.33%) | 54 (90.0%) | 3 (5.0%) |
| | Batch 6 (61 cases) | 55 (90.16%) | 56 (91.8%) | 2 (3.28.92%) |
| Embodiment 2 (184 cases) | Batch 1 (60 cases) | 56 (93.33%) | 56 (93.3%) | 2 (3.33%) |
| | Batch 3 (62 cases) | 58 (93.55%) | 58 (93.55%) | 2 (3.23%) |
| | Batch 5 (62 cases) | 58 (93.55%) | 59 (95.16%) | 2 (3.23%) |
| Comparative Example (179 cases) | Batch 1 (60 cases) | 52 (86.67%) | 51 (85.00%) | 3 (5.0%) |
| | Batch 2 (59 cases) | 51 (86.44%) | 51 (86.44%) | 3 (5.08%) |
| | Batch 3 (60 cases) | 52 (86.67%) | 52 (86.67%) | 3 (5.0%) |
| Blank control (62 cases) | | 38 (61.29%) | 40 (64.52%) | 10 (16.13%) |

TABLE 21

| | | | Increased | Hypogastrium | Endometrial |
| | | Endometrial | secretion | bearing-down pain | adhesion |
| Batch (number of cases) | | thickness/mm | (proportion %) | (proportion %) | (proportion %) |
| --- | --- | --- | --- | --- | --- |
| B-ultrasonic examination recovery comparison | | | | | |
| Embodiment 1 (183 cases) | Batch 1 (62 cases) | 6.58 ± 0.86 | 4 (6.45%) | 6 (9.68%) | 3 (4.84%) |
| | Batch 3 (60 cases) | 6.64 ± 0.53 | 3 (5.0%) | 5 (8.33%) | 3 (5.0%) |
| | Batch 6 (61 cases) | 6.92 ± 0.49 | 3 (4.92%) | 5 (8.2%) | 2 (3.28%) |
| Embodiment 2 (184 cases) | Batch 1 (60 cases) | 7.08 ± 0.58 | 2 (3.33%) | 3 (5.0%) | 2 (3.33%) |
| | Batch 3 (62 cases) | 7.02 ± 0.44 | 3 (4.84%) | 3 (4.84%) | 2 (3.23%) |
| | Batch 5 (62 cases) | 7.14 ± 0.49 | 2 (3.23%) | 2 (3.23%) | 2 (3.23%) |
| Comparative Example (179 cases) | Batch 1 (60 cases) | 5.46 ± 0.62 | 6 (10.0%) | 6 (10.0%) | 4 (6.67%) |
| | Batch 2 (59 cases) | 5.59 ± 0.31 | 6 (10.17%) | 6 (10.17%) | 3 (5.08%) |
| | Batch 3 (60 cases) | 5.68 ± 0.5 | 5 (8.33%) | 6 (10%) | 3 (5.0%) |
| Blank control (62 cases) | | 4.31 ± 0.24 | 19 (30.65%) | 18 (29.03%) | 15 (24.19%) |

From the data in Tables 19-21, it can be seen that compared to the original Fuke Qianjin Capsules that only control the active ingredient of *Herba andrographis*, the Fuke Qianjin Capsules of the present invention that the contents of genistin, and/or jatrorrhizine, and/or palmatine, and/or berberine are controlled, the effectiveness of the Fuke Qianjin Capsules in the treatment of endometritis is improved. The specific performance is that the efficiency and the markedly effective rate have been improved, indicating that when the contents of genistin, and/or jatrorrhizine, and/or palmatine, and/or berberine are controlled, the Fuke Qianjin Capsules can interact better with antibiotics and progesterone.

From the consistency experiment of the above Embodiments and Comparative Example, it can be seen that in the production process, the detection of the ingredients of the mixed cream sample is added, and the control is within a reasonable range, so that the contents of the eight active ingredients in the obtained Fuke Qianjin Capsules can be controlled within a reasonable and narrow range, so that the consistency between batches of the prepared product is better, and the clinical treatment effect is improved.

Finally, it should be noted that the above Embodiments are only used to illustrate the technical solution of the present invention and not to limit the scope of protection of the present invention. For those of ordinary skill in the art, on the basis of the above description and ideas, other different forms of changes or variations can also be made, and it is not necessary and impossible to enumerate all the implementation here. All modifications, equivalent replacements and improvements made within the spirit and principles of the present invention shall be included in the scope of protection claimed in the present invention.

What is claimed is:

1. A quality control method for Fuke Qianjin Capsules, wherein the quality control method comprises the following steps:

using *Radix et caulis flemingiae*, *Radix rosa laevigata*, *Herba andrographis*, *Radix angelicae sinensis*, *Caulis mahoniae*, *Zanthoxylum dissitum* Hemsl., *Caulis spatholobi* and *Radix codonopsis* as raw materials;

S1, first obtaining a *Radix angelicae sinensis* residue and a liquid medicine by ethanol percolating the *Radix angelicae sinensis* and extracting the liquid medicine to prepare a cream;

S2, obtaining a *Herba andrographis* residue and a liquid medicine by ethanol refluxing the *Herba andrographis* and extracting the liquid medicine to prepare a cream;

S3, boiling and extracting the *Caulis mahoniae* and the *Zanthoxylum dissitum* Hemsl. with water twice, after filtering, obtaining a *Caulis mahoniae* and *Zanthoxylum dissitum* Hemsl. residue and two filtrates, and combining the two filtrates to prepare a cream;

S4, boiling and extracting the *Radix et caulis flemingiae*, the *Radix rosa laevigata*, the *Caulis spatholobi*, and the *Radix codonopsis* with water once and then filtering to obtain a residue, boiling with water the filtered residue with the *Radix angelicae Sinensis* residue produced in the step S1, the *Herba andrographis* residue produced in the step S2 and the *Caulis mahoniae* and *Zanthoxylum dissitum* Hemsl. residue produced in the step S3 together, filtering, combining filtrates to prepare a cream; and S5, combining the four creams of the steps S1, S2, S3, S4, mixing to obtain a mixed cream, detecting contents of the Z-ligustilide, the Z-3-butylidenephthalide, the genistin, the jatrorrhizine, the palmatine, the berberine, and a total amount of the andrographolide and the dehydroandrographolide in the mixed cream by a HPLC, controlling the content of Z-ligustilide, the content of genistin, the content of palmatine, the content of berberine, and the total amount of andrographolide and dehydroandrographolide in the mixed cream to reach a predetermined content, spray drying, and then pelletizing, encapsulating to obtain the Fuke Qianjin Capsules, Wherein a content of each Fuke Qianjin Capsule is 0.4 g, and the predetermined content is controlled according to following range: each of the Fuke Qianjin Capsules contains 0.04 mg to 0.06 mg of the genistin, 0.090 mg to 0.130 mg of the palmatine, 0.13 mg to 0.18 mg of the berberine, 3.0 mg to 3.65 mg of the Z-ligustilide, and the total amount of the andrographolide and the dehydroandrographolide is not less than 3.5 mg.

2. The quality control method for the Fuke Qianjin Capsules according to claim 1, wherein in the step S5, per milligram of the mixed cream, the content of the genistin is not less than 0.00015 mg, the content of the jatrorrhizine is not less than 0.0004 mg, the content of the palmatine is not less than 0.00038 mg, the content of the berberine is not less than 0.0004 mg, the content of the Z-ligustilide is not less than 0.01 mg, the content of the Z-3-butylidenephthalide is not less than 0.00017 mg, and the total amount of the andrographolide and the dehydroandrographolide is not less than 0.01 mg.

3. The quality control method for the Fuke Qianjin Capsules according to claim 2, wherein in the step S5, it is controlled that per milligram of the mixed cream, the content of the genistin is 0.0025 mg to 0.0035 mg, the content of the jatrorrhizine is 0.009 mg to 0.015 mg, the content of the palmatine is 0.007 mg to 0.01 mg, the content of the berberine is 0.0085 mg to 0.01 mg the content of the Z-ligustilide is 0.0165 mg to 0.022 mg, the content of the Z-3-butylidenephthalide is 0.00036 mg 0.0006 mg, and the total amount of the andrographolide and the dehydroandrographolide is not less than 0.02 mg.

4. The quality control method for the Fuke Qianjin Capsules according to claim 2, in the step S5, per milligram of the mixed cream, the content of the genistin is not less than 0.0002 mg, the content of the jatrorrhizine is not less than 0.0006 mg, the content of the palmatine is not less than 0.0006 mg, the content of the berberine is not less than 0.0006 mg, the content of the Z-ligustilide is not less than 0.015 mg, the content of the Z-3-butylidenephthalide is not less than 0.00025 mg, and the total amount of the andrographolide and the dehydroandrographolide is not less than 0.015 mg.

5. The quality control method for the Fuke Qianjin Capsules according to claim 1, wherein a detection method adopted in the step S5 is HPLC detection;

a detection process described in the step S5 is: taking 1 g mixed cream, adding 200 mL of 75% formalin to dissolve and obtaining a dissolving solution, and then taking 2 mL of the dissolving solution, ultrasonically extracting with 75% formalin for (30±5) minutes, after cooling to room temperature, using 75% formalin to make up a mass loss, passing through a 0.45 μm microporous membrane, and taking the filtrate as a solution to be tested;

conditions of the HPLC detection in the step S5 is as follows: using Kromasil 100-5-C18 chromatographic column, with mobile phases using acetonitrile as an A phase and 0.1% phosphoric acid aqueous solution as a B phase, gradient eluting, with a flow rate being 1.0 mL·min-1, a detection wavelength being 254 nm, a column temperature being (30±0.5)° C., and an injection volume being 10 μL;

in the step S5, said controlling is performed by adjusting an extraction process of the steps S1, S2, S3, S4 or a source of the raw materials.

* * * * *